United States Patent [19]

Wiesner et al.

[11] 4,380,624

[45] Apr. 19, 1983

[54] NOVEL ISOMERS OF BUFALIN AND RESIBUFOGENIN AND THEIR PREPARATION

[75] Inventors: Karel Wiesner; Thomas Y. R. Tsai, both of Fredericton, Canada

[73] Assignee: Advance Biofactures Corp., Lynbrook, N.Y.

[21] Appl. No.: 288,763

[22] Filed: Jul. 31, 1981

[51] Int. Cl.$^3$ .................... A61K 31/705; A61K 31/58
[52] U.S. Cl. ..................................... 536/5; 260/239.57
[58] Field of Search ........................ 260/239.57; 536/5

[56] References Cited

U.S. PATENT DOCUMENTS 4,031,212  6/1977  Losel et al. ...................... 260/239.57
4,218,447  8/1980  Isaac et al. ...................... 260/239.57
4,242,332  12/1980 Albrecht et al. ......................... 536/5

OTHER PUBLICATIONS

"Steroids" by Fieser et al., (New York), Reinhold Publishing Corporation, pp. 792–795.

Primary Examiner—Elbert L. Roberts
Attorney, Agent, or Firm—Roland Plottel

[57] ABSTRACT

This invention relates to novel isomers of naturally occurring cardiotonic compounds, specifically novel isobufalins and novel isoresibufogenins. This invention also relates to a novel method of preparing the novel isomers.

14 Claims, No Drawings

NOVEL ISOMERS OF BUFALIN AND RESIBUFOGENIN AND THEIR PREPARATION

BACKGROUND OF THE INVENTION

1. Field of the Invention

This invention relates to novel isomers of bufalin and resibufogenin and their glycosides. In particular, this invention relates to the preparation of these compounds and their use in the treatment of various heart diseases.

2. Description of Prior Art

Bufalin and resibufogenin are examples of compounds within the class of compounds known as aglycones, or genins. The aglycones are steroid derivatives which exert a strong, specific action on the heart muscle in man or animals; they are consequently characterized as being cardiac-active or cardiotonic. These compounds have found important use, particularly in their glycosidic form, in the treatment of heart diseases by, for instance, exerting a beneficial stimulation to a diseased heart. The glycosides are known as cardiac glycosides.

The aglycones are characterized by a steroid nucleus with methyl substituents at the 10 and 13 positions, a hydroxy substituent normally at the 14 position, and a substituent at the 17 position which is either a five-membered α,β unsaturated lactone ring or a six-membered, twice-unsaturated lactone ring. The steroid nucleus is of the cis-decalin type, with trans B/C ring structure and cis C/D ring structure. The hydroxy groups and methyl groups are β oriented.

The aglycones containing the five-member lactone substituent are known as cardenolides. A description of certain cardenolides and their preparation is found in U.S. Pat. No. 4,259,240, entitled "Synthesis of Furyl Intermediates, and Cardenolides and Their Isomers Prepared Therefrom," the disclosure of which is incorporated herein by reference. Cardenolides occur naturally in plants. Digitalis, for instance, is a mixture of cardenolide glycosides which, upon hydrolysis, affords a mixture of cardenolides, including digitoxigenin, digoxigenin and gitoxigenin.

Digitalis preparations have been used in the treatment of heart disease for more than 200 years. The cardiotonic glycosides contained in these preparations have the ability to slow the heart rate and, at the same time, to increase the contractility of the heart muscle (that is, they display inotropic activity), and thus to improve, in general, the heart function. The inotropic effect, on the biochemical level, is connected to the release of calcium. Because of these characteristics, the glycosides of digitalis are among the top ten most prescribed drugs.

The aglycones containing the six-member lactone substituents are known as bufadienolides. They occur naturally in plants and animals, and, like the cardenolides, possess high inotropic activity. Bufalin is a bufadienolide found naturally in certain toads, the formula of which, identical in nuclear structure to digitoxigenin, is shown below.

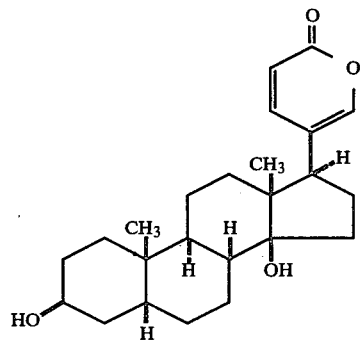

Bufalin

Resibufogenin, shown below, also a naturally occurring bufadienolide found in certain toads, contains a 14,15 epoxy linkage in place of the 14-hydroxy group.

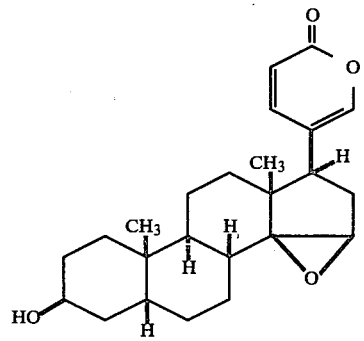

Resibufogenin

The aglycones, both cardenolides and bufadienolides, are often found in nature in their glycosidic form, with the aglycone moiety linked to a sugar at the 3-position of the steroid nucleus. The glycosidic form is normally employed in clinical applications, the sugar residue providing favorable solubility and distribution characteristics. Analysis of naturally occurring aglycone glycosides has shown the presence of a large variety of different sugars, including glucose, rhamnose, fucose, talomethlose, antiarose, allomethylose, thevetose, digitalose, acovenose, acofriose, cymarose, sarmentose, oleandrose, diginose, digitoxose, and boivinose.

With respect to methods of preparing and manipulating 17-substituted steroid compounds, U.S. Pat. No. 4,259,240 discloses reaction of a 15,16 unsaturated, 17-keto testosterone derivative to give a 17-β-hydroxy, 17-α-furyl compound. This compound is subjected to allylic rearrangement to yield a 16,17 unsaturated, 15-hydroxy, 17-β-furyl product. Subsequent steps include saturation of the 16,17 double bond; dehydroxylation of the 15-hydroxy to yield a 14,15 double bond; and addition of a 14-β-hydroxy to the double bond.

With respect to the possibility of converting furanes into six-membered rings, oxidative ring openings of furanes to furanose sugar derivatives and tautomerizations of these to pyranose derivatives are well known in furane and sugar chemistry. However, the ring opening of the 17-furyl substituent of the invention is part of the key to the preparation of the novel isomers, and is unknown in the art.

A major problem with the clinical application of aglycones is the dangerously high toxicity of these compounds. In fact, many of these compounds have found historical use as poisons. In the clinical use of digitalis glycosides, for instance, most patients are given 60% of the toxic dose in order to obtain the desired therapeutic response. As a consequence, the margin of safety is quite narrow and, by some estimates, digitalis glycosides are responsible for one-half of all drug-induced hospital deaths. Bufadienolide glycosides are similarly quite toxic unless administered in carefully controlled dosages.

Another problem in the clinical use of cardiac glycosides is the scarcity, and consequent expense, of many of these compounds. Bufalin, for instance, is currently used clinically even though it has not been synthesized and must be isolated from natural sources at a cost of several thousand U.S. dollars per gram.

SUMMARY OF THE INVENTION

In accordance with the invention, novel isomers of bufalin and resibufogenin are prepared which have important clinical application in their glycosidic form, by virtue of their having a superior combination of cardiotonic activity and decreased toxicity.

The novel isomers of bufalin, a first isobufalin, hereinafter isobufalin (a), and a second isobufalin, hereinafter isobufalin (b), are shown, respectively, in Formulas I and II.

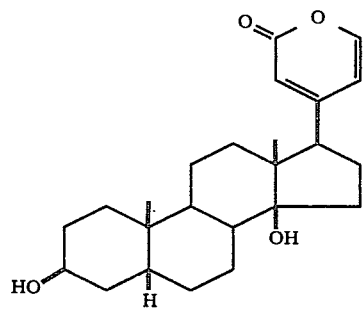

Isobufalin (a)

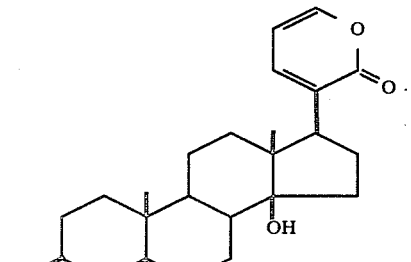

Isobufalin (b)

The novel glycosides of the novel isomers of bufalin, isobufalin (a) glycoside and isobufalin (b) glycoside, are shown, respectively, in Formulas III and IV, where S is a sugar.

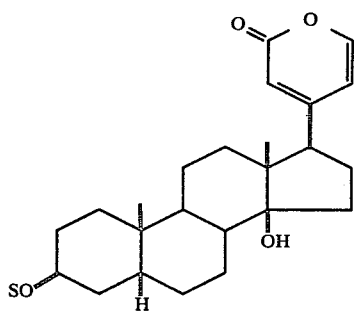

Isobufalin (a) Glycoside

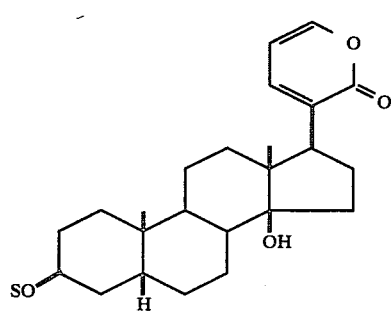

Isobufalin (b) Glycoside

The novel isomers of resibufogenin, a first isoresibufogenin, hereinafter isoresibufogenin (a), and a second isoresibufogenin, hereinafter isoresibufogenin (b), are shown, respectively, in Formulas V and VI.

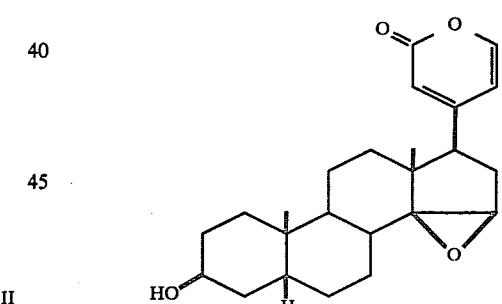

Isoresibufogenin (a)

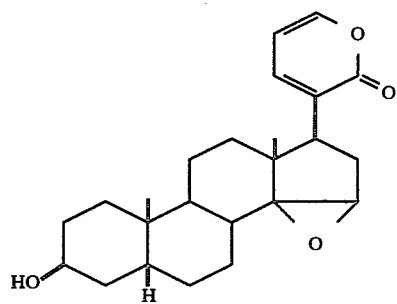

Isoresibufogenin (b)

The novel glycosides of the novel isomers of resibufogenin, isoresibufogenin (a) glycoside and isoresibufogenin (b) glycoside, are shown, respectively, in Formulas VII and VIII, where S is a sugar.

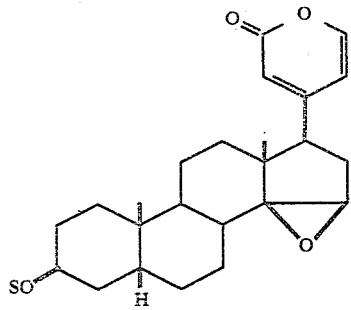

Isoresibufogenin (a) Glycoside

VII

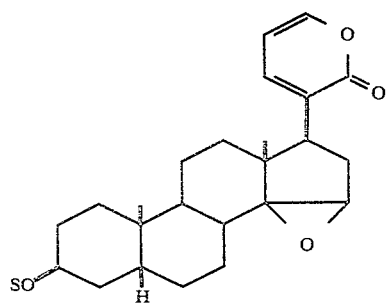

Isoresibufogenin (b) Glycoside

VIII

The novel compounds of the invention are not found naturally and have not been previously synthesized.

The invention includes a novel method of preparing the isobufalin and isoresibufogenin isomers, whereby a diether-substituted furyl group is added to a 15,16 unsaturated, 17-keto steroid to yield a 17-β-hydroxy, 17-α-furyl compound. Allylic rearrangement results in a 16,17 unsaturated, 15-hydroxy, 17-β-furyl steroid. After the diether substituent is converted to a hydromethylene substituent, the furyl ring is subjected to oxidative ring opening to yield a 17-β six-membered pyrane product. This product is then converted in a series of steps to the ultimate isomer products.

This method of preparation constitutes a unique combination of allylic rearrangement and furyl ring expansion which allows the synthesis of the previously unprepared isomers of the invention. This method permits the correct stereo-positioning of the substituents of the novel isomers, in particular the 17-β-pyrane and the 15-β-hydroxy (or 14,15-β-epoxy) substituents, which positioning is necessary to the cardiotonic activity of the isomers.

The method of the invention, as it applies to the preparation of isobufalin (a), is carried out in the following manner:

(a) reacting a compound of Formula I (Compound 1)

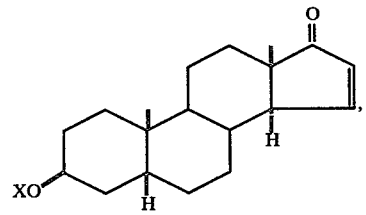

wherein X is a blocking group, with an anion of formula

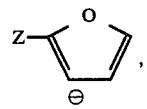

where Z is selected from the group consisting of

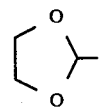

and CH₃—O—CH₂—O—CH₂—, to produce a tertiary alcohol of Formula 2 (Compound 2)

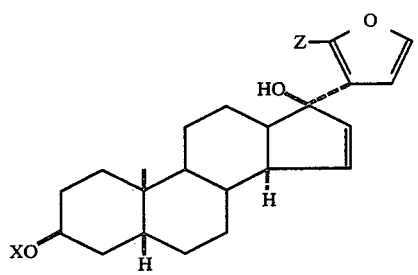

(b) acetylating Compound 2 at the 17-position and subjecting the resulting 17-acetate to a stereospecific allylic rearrangement to produce an allylic alcohol of Formula 3 (Compound 3)

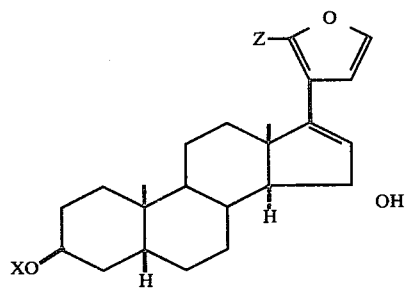

(c) selectively hydrogenating the 16, 17 double bond of Compound 3 to produce a 16,17 saturated ketal of Formula 4 (Compound 4)

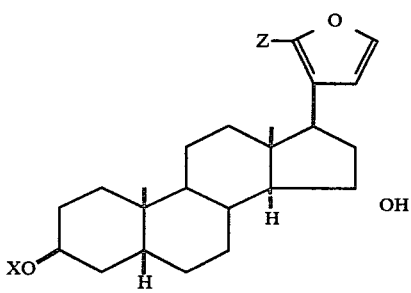

4

(d) hydrolyzing Compound 4 to produce a furyl aldehyde of Formula 5 (Compound 5)

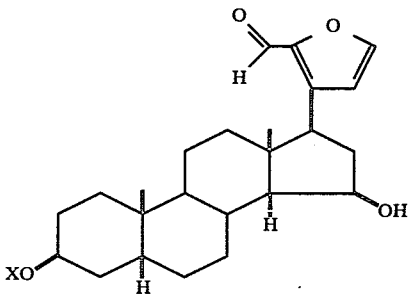

5 and then reducing Compound 5 to produce a furyl methylene alcohol of Formula 6 (Compound 6)

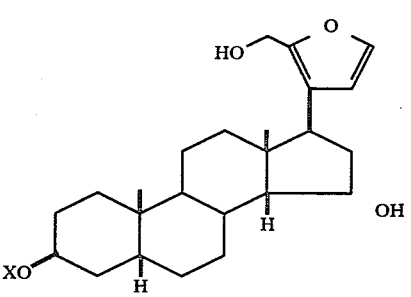

6 and, (e) oxidizing Compound 6 with a peracid to produce a ketohemiacetal of Formula 7 (Compound 7).

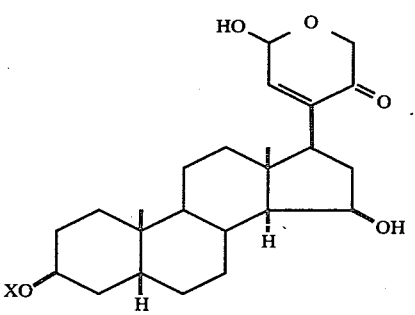

7

At this point the 17-pyrane ring is in the proper β-orientation and the 15-hydroxy group provides the means to bring about the ultimate positioning of the 14-β-hydroxy (or 14,15-β-epoxy). All that remains to obtain the final isobufalin product is to rearrange the substituents on the pyrane ring and to position the 14-β-hydroxy group. The method of the invention embraces more than one means of proceeding from Compound 7 to the final isobufalin product, a preferred synthetic route being the carrying out of the subsequent series of reaction steps shown below.

(f) substituting the 23-hydroxy group of Compound 7 with a hydrolyzable blocking group X' to give a compound of Formula 8 (Compound 8)

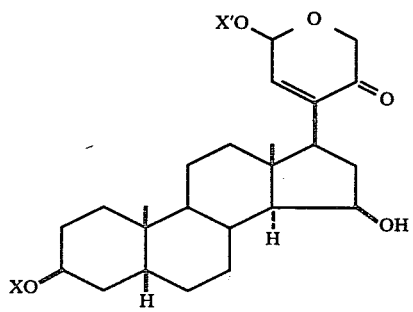

8 next, selectively dehydrating Compound 8 at the 15-position to produce a 14,15-unsaturated compound having Formula 9 (Compound 9),

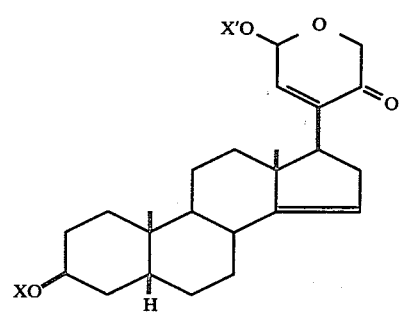

9 and selectively hydrolyzing Compound 9 to produce a 23-hydroxy compound of Formula 10 (Compound 10)

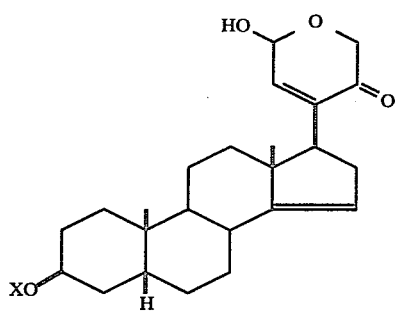

10

(g) oxidizing Compound 10 to produce a keto lactone intermediate, and reducing said intermediate to produce a hydroxy lactone of Formula 11 (Compound 11)

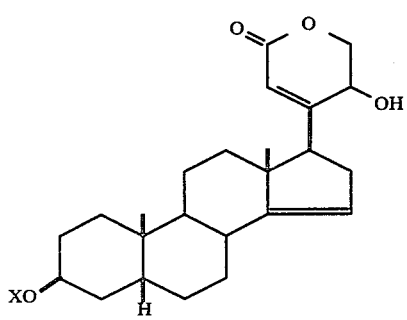

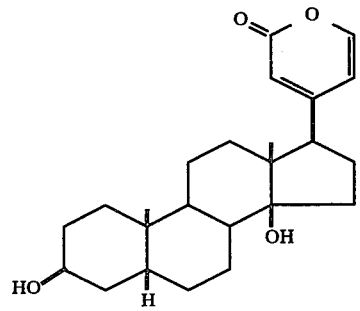

(h) dehydrating the 21-hydroxylactone of Compound 11 either in a single step to give Compound 13 directly or, preferably, in a two-step sequence of first substituting the hydroxy with a leaving group X″ to produce a substituted product of Formula 12 (Compound 12)

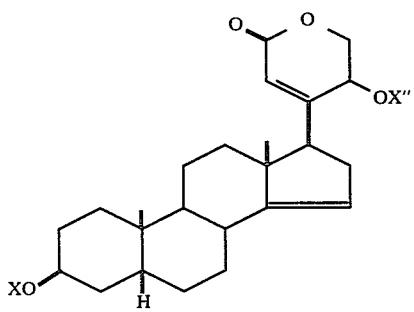

and, second, eliminating the leaving group to produce a pyrone derivative having Formula 13 (Compound 13)

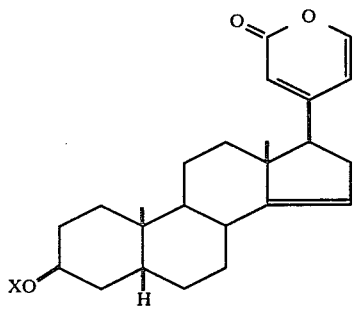

(i) hydroxylating Compound 13 at the 14-position to produce a precursor of isobufalin (a) having Formula 14 (Compound 14)

(j) selectively converting the 3-position blocking group of Compound 14 into a hydroxy group, thereby yielding isobufalin (a), which is Compound I.

In accordance with the invention, isobufalin (b), Formula II, is synthesized in a manner analogous to the synthesis of isobufalin (a), but using a different anion in the first step of the synthesis. The synthesis is accomplished by carrying out the following steps:

(a) reacting Compound 1 with an anion of formula

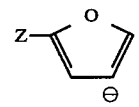

, where Z is Z is selected from the group consisting of

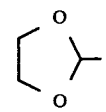

and $H_3C\text{-}O\text{-}CH_2\text{-}O\text{-}CH_2\text{-}$, to produce a tertiary alcohol of Formula 15 (Compound 15)

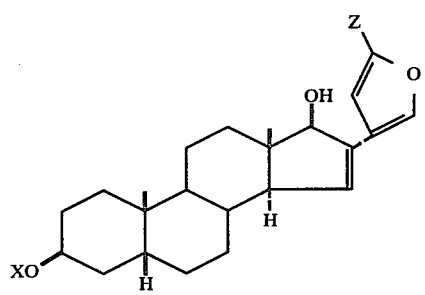

(b) acetylating Compound 15 and subjecting the resulting 17-acetate to a stereospecific allylic rearrangement to produce an allylic alcohol of Formula 16 (Compound 16)

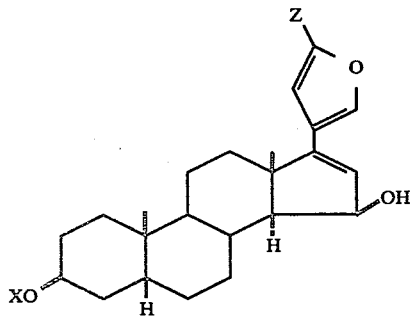

(c) selectively hydrogenating the 16,17 double bond of Compound 16 to produce a 16,17 saturated ketal of Formula 17 (Compound 17)

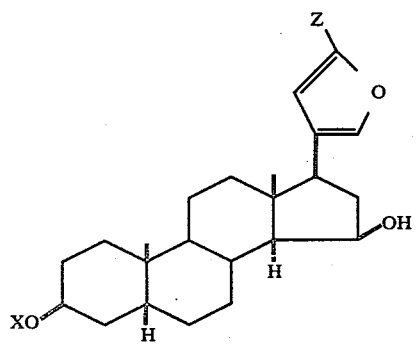

(d) hydrolyzing Compound 17 to produce a furyl aldehyde of Formula 18 (Compound 18)

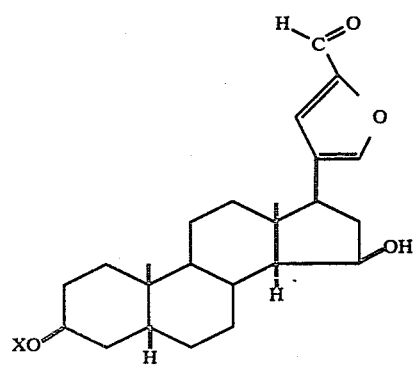

and then reducing Compound 18 to produce a furyl methylene alcohol of Formula 19 (Compound 19)

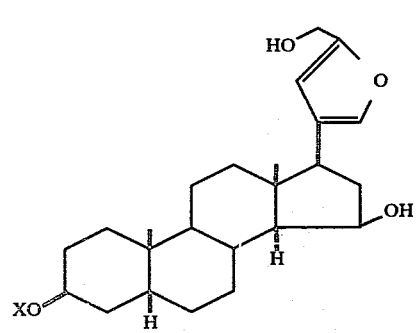

and, (e) oxidizing Compound 19 to produce a ketohemiacetal of Formula 20 (Compound 20)

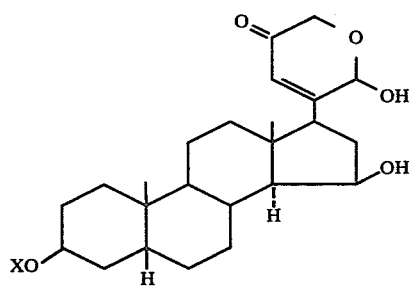

At this point the 17-pyrane ring is in the proper $\beta$-orientation and the 14-hydroxy group provides the means to bring about the ultimate positioning of the 15-$\beta$-hydroxy (or 14,15-$\beta$-epoxy). All that remains, as in the synthesis of the isobufalin (a) isomer, to obtain the final isobufalin product is to rearrange the substituents on the pyrane ring and to position the 14-$\beta$-hydroxy group. The method of the invention embraces more than one means of proceeding from Compound 20 to the final isobufalin product, a preferred synthetic route being the carrying out of the subsequent series of reaction steps shown below.

(f) substituting the 21-hydroxy group of Compound 20 with a hydrolyzable blocking group X' to give a compound of Formula 21 (Compound 21)

next, selectively dehydrating Compound 21 at the 15-position to produce a 14,15 unsaturated compound of Formula 22 (Compound 22)

and selectively hydrolyzing Compound 22 to produce a 21-hydroxy compound of Formula 23 (Compound 23)

(g) oxidizing Compound 23 to produce a keto lactone intermediate, and reducing said intermediate to produce a hydroxy lactone of Formula 24 (Compound 24)

(h) dehydrating the 23-hydroxy of Compound 24 either in a single step to give Compound 26 directly or, preferably, in a two-step sequence of first substituting the hydroxy with a leaving group X" to produce a compound of Formula 25 (Compound 25)

and, second eliminating the leaving group to produce a pyrone derivative of Formula 26 (Compound 26)

(i) hydroxylating Compound 26 at the 14-position to produce a precursor of isobufalin (b) of Formula 27 (Compound 27)

and, (j) selectively converting the 3-position blocking group of said precursor into a hydroxy group, thereby yielding isobufalin (b), which is Compound II.

In accordance with the invention, isobufalin (a) and isobufalin (b) are converted to the corresponding novel glycosides by reaction with a sugar. The sugar can be any one of a large number of sugars, either monosaccharide or polysaccharide. Monosaccharide sugars are preferred, with glucose being particularly preferred.

In accordance with the invention, isoresibufogenin (a), which is Compound V, is synthesized by carrying out steps (a)–(h) above for the synthesis of the isobufalin (a), followed by carrying out the following additional steps: first, epoxidizing Compound 13 to produce the epoxy compound of Formula 28 (Compound 28)

and, second, selectively hydrogenating Compound 28 to produce isoresibufogenin (a).

In accordance with the invention, isoresibufogenin (b), which is Compound VI, is synthesized in a manner analogous to the synthesis of isoresibufogenin (a), but using a different anion in the first step of the synthesis. The synthesis is accomplished by carrying out steps (a)–(h) above for the synthesis of isobufalin (b), followed by carrying out the following additional steps: first, epoxidizing Compound 26 to produce the epoxy compound of Formula 29 (Compound 29)

and, second, selectively hydrogenating Compound 29 to produce isoresibufogenin (b).

In accordance with the invention, isoresibufogenin (a) and isoresibufogenin (b) are converted to the corresponding novel glycosides by reaction with a sugar. The sugar can be any one of a large number of sugars, either monosaccharide or polysaccharide. Monosaccharide sugars are preferred, with glucose being particularly preferred.

The novel bufalin and resibufogenin compounds of this invention have utility in the clinical treatment of animal and human heart disorders. These compounds, and in particular their glycosides, are to be used clinically in accordance with standard modes of administration known in the art, such as in the clinical administration of bufalin, digitalis and related cardiotonics. Dosage and method of administration, intravenous or oral, will depend on the clinical circumstances, but will be determinable, without undue experimentation, by one skilled in the art.

While the novel bufalin and resibufogenin isomers of this invention may be used in the non-glycosidic state, the glycosidic form is preferred for clinical use. A variety of sugars can be employed as the sugar residue of the glycoside, as will be well understood by those skilled in the art. Either monosaccharides or polysaccharides can be used with monosaccharides being preferred and glucose being particularly preferred.

The novel cardiac-active compounds of the invention are of clinical importance in view of their superior combination of cardiotonic activity and decreased toxicity. These properties were predicted by structure-activity relationships based on model systems. The clinical availability of cardio-active compounds of decreased toxicity will offset the previously discussed major problems associated with the cardiotonic agents currently in use. Specifically, the problems of narrow margin of safety and high incidence of toxic reaction or death may be dealt with.

Furthermore, the availability of the compounds of the invention, as readily prepared by the method of the invention, is of particular importance in view of the scarcity and expense of the cardiac glycosides currently in use.

DETAILED DESCRIPTION

The preparation of the novel compounds of the invention is based on a series of important steps. Key among these are the stereospecific allylic rearrangement step which leads to the positioning of the 17-$\beta$-furyl and the 14-hydroxy groups (in the case of isobufalin (a), this is the conversion of Compound 2 to Compound 3), and the furane oxidation step which permits expansion of the five-member furane ring into a six-member pyrane ring (in the case of isobufalin (a), this is the conversion of Compound 6 to Compound 7). The 15-hydroxy group is subsequently dehydrated to yield a 14,15-double bond that in turn can be reacted to give the 14-$\beta$-hydroxy group (or, for the isoresibufogenins, the 14,15-$\beta$-epoxy group).

The preparation of the novel compounds by the method of this invention yields products with the correct stereo-positioning, which corresponds to that found in the naturally occurring bufalin and resibufogenin and which is necessary for proper cardiotonic activity. Specifically, the preparation method of the invention yields a steroid nucleus of the cis-decalin type with 3-$\beta$-OH, 5-$\beta$-H, 8-$\beta$-H, 9-$\alpha$-H, 10-$\beta$-Me, 13-$\beta$-Me, 14-$\beta$-OH and 17-$\beta$-pyrone. The $\beta$-orientation is shown herein by a solid line whereas the $\alpha$-orientation is shown by a dotted line.

The method of preparing isobufalin (a) will be described, and may be considered a model for the methods of preparing the other novel compounds. Isoresibufogenin (a) is prepared in the same manner as isobufalin (a), except for the conversion, in the penultimate step, of the 14,15-double bond into a 14,15-epoxy group. Isobufalin (b) is prepared strictly analogously to isobufalin (a), except the furyl anion used in the first step of the sequence has a different reactive site, resulting in attachment to the steroid nucleus at the furyl 3-position, instead of the furyl 2-position. Isoresibufogenin (b) is prepared in the same manner as isobufalin (b), except for the conversion, in the penultimate step, of the 14,15 double bond to a 14,15-epoxy group instead of a 14-OH group. The glycosides of the novel compounds are prepared by straightforward substitution of the 3-hydroxy with the appropriate sugar group, as will be understood by those skilled in the art.

In the method of preparing isobufalin (a), the starting material is Compound 1, a steroidal ketone containing a suitable hydrolyzable blocking group at the 3-position (shown as X in Formula 1). The methyl groups, blocking group, and 5-hydrogen are $\beta$-oriented; the 14-hydrogen is $\alpha$-oriented. Suitable blocking groups will be known to those skilled in the art, such as paramethoxybenzyl and tertiary butyl, with benzyl being preferred. Compound 1, where X is benzyl, is known in the art and may be readily prepared from testosterone or other well-known steroids. An 11-step preparation from testosterone is disclosed in U.S. Pat. No. 4,259,240 (columns 4–6).

Compound 1 is converted to Compound 2 by reaction with a substituted organometallic furyl reagent, where the substituent is either the cyclic diether

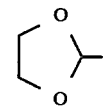

or the linear diether CH$_3$—O—CH$_2$—O—CH$_2$—. The cyclic-diether furyl reagent is prepared by reaction of 2-acetal-3-bromo furan with n-butyl lithium, as shown below, but other organometallic compounds could be similarly employed.

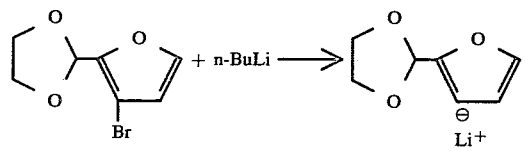

The linear-diethyl furyl reagent is prepared by reacting the corresponding linear-diether bromo furyl compound with the organometallic compound. Organometallic compounds such as here described are disclosed in copending application Ser. No. 193,175 of Wiesner, Mar, Tsai and Tsai, filed Oct. 1, 1980, the disclosure of which is incorporated herein by reference.

The conversion of Compound 1 to Compound 2 using the organometallic furyl reagent is carried out in an ether solution. Diethyl ether is preferred, but other ethers can be employed such as dioxane or tetrahydrofuran.

Compound 2 has a tertiary alcohol group at the 17-position, the 17-hydroxy group being in the β-orientation. Compound 2 is converted to Compound 3 in a two-step process. In the first step, Compound 2 is acetylated at the 17-position under standard acetylating conditions for hindered hydroxyls. Conditions of choice are acetic acid in pyridine. Other acetylating reagents could be used, such as acetyl chloride. In the second step the acetate, which need not be purified, is subjected to an allylic rearrangement in basic solution. A variety of organic solvents and bases may be employed, with acetone and calcium carbonate being the preferred system. Other bases of choice include potassium carbonate, silica gel, and alumina.

The allylic rearrangement yields Compound 3, which contains a 17-furyl group, a 15-β-hydroxy group, and 16,17 unsaturation. Stereospecific selective hydrogenation of the 16,17 double bond brings about conversion of Compound 3 to Compound 4, with creation of the β-orientation of the 17-substituent. Hydrogenation is carried out over a catalyst. Appropriate catalysts are known to those skilled in the art; in this system a catalyst must be chosen which selectively hydrogenates the 16,17 double bond but not the 3-substituent. A preferred catalyst is Pd/CaCO₃. Other hydrogenation catalysts from the platinum metal group could be used.

Compound 4 is hydrolyzed to Compound 5 under standard acid conditions. A variety of acids either mineral or organic, e.g. acetic, may be chosen, with HCl in THF being an acid system of choice. The reaction hydrolyzes the substituent (the Z group) on the furyl ring to yield an aldehyde group at that site. The reaction proceeds similarly irrespective of whether the Z group is the cyclic diether or the linear diether.

The aldehyde group of Compound 5 is reduced to the corresponding alcohol group, to yield Compound 6, using any one of a number of sets of conditions known to those skilled in the art to bring about aldehyde to alcohol reductions. NaBH₄ in THF/MeOH is a reducing system of choice, but other complex hydride reducing agents could also be used.

Compound 6 is subjected to oxidative ring opening to convert the five-member furyl substituent into a six-member ring substituent, thereby yielding Compound 7. A number of oxidizing agents could be employed, with hydrogen peroxide or peracids being preferred. The oxidizing agent of choice is m-chloroperbenzoic acid. Alternatively, the oxidation could be done electrolytically. It is believed that Compound 6 is initially converted by the oxidizing agent into the following intermediate, a furanose derivative, which is not isolated.

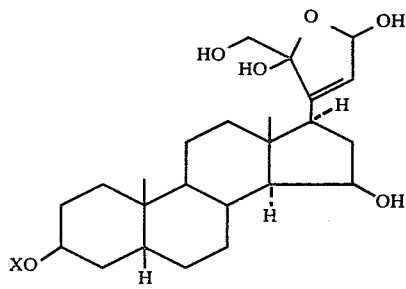

The intermediate is believed to immediately isomerize to the pyrane, Compound 7.

In accordance with the preferred route for converting Compound 7 to the final product, the 23-hydroxy group of Compound 7 is at this point protected by selectively adding a blocking group (X') to the 23-position, thereby producing Compound 8. The presence of the blocking group permits the dehydroxylation of the 15-hydroxy in the subsequent step. A number of blocking groups could be employed, as will be understood by those skilled in the art, with acetate being a blocking group of choice. The 23-position can be conveniently acetylated under conditions known to those skilled in the art. Under the proper conditions the 15-hydroxy group, which is less susceptible to acetylation, does not react.

Dehydroxylation of the 15-hydroxy of Compound 8 yields the 14,15 unsaturated Compound 9. Dehydroxylation may be accomplished with any one of a number of dehdroxylating agents known to those skilled in the art. Thionyl chloride is an agent of choice. Alternatively, a two-step dehydroxylation could be used, such as tosylation followed by treatment with base.

The blocking group at the 23-position of Compound 9 is reconverted to a hydroxy group by selective hydrolysis under basic conditions to yield Compound 10. A variety of basic conditions may be employed, with an inorganic hydroxide system, such as KOH, being preferred.

In order to properly position the keto group on the six-member 17-substituent, Compound 10 is reacted with an appropriate oxidizing agent, such as MnO₂ or CrO₃, with the latter being preferred, to yield initially, it is believed, the following non-isolated keto lactone intermediate.

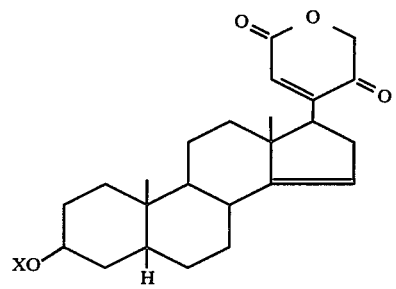

The above intermediate compound is reduced with an appropriate reducing agent such as Na(BH₄) or, preferably, Zn(BH₄)₂ to yield the 23-keto Compound 11.

Dehydroxylation of Compound 11 at the 21-position is accomplished by initial substitution of the 21-hydroxy with an appropriate leaving group (X''), the mesyl or tosyl group being preferred, to yield Compound 12. The leaving group is then eliminated under relatively strongly basic conditions, for example, in the presence of DBN (diazabicyclonon-5-ene [4.3.0]), to yield Compound 13, a derivative of α-pyrone. Other bases which could be used include tetramethyl guanidine and quinuclidine. Alternatively, the dehydroxylation of Compound 11 could be accomplished in a single step with a suitable dehydroxlating agent, for instance thionyl chloride.

Compound 13 is readily converted to isobufalin (a) in two steps. First, Compound 13 is stereospecifically hydroxylated at the 14-position to yield Compound 14, which contains a 14-β-hydroxy group. An appropriate stereospecific hydroxylating system is employed, with N-bromosuccinimide (NBS) or N-bromoacetamide, together with Raney nickel, being a system of choice. Bromohydrin intermediates are involved in such hydroxylation reactions. In the second step Compound 14 is converted to isobufalin (a) by hydroxylation of the 3-position blocking group. This is best accomplished by selective catalytic hydrogenation using an appropriate hydrogenation catalyst. Pd/C is a preferred catalyst, but other catalysts from the platinum group can also be used.

Isoresibufogenin (a) is prepared in the same manner as isobufalin (a), except Compound 13 is converted to Compound 28 by reaction with an appropriate epoxidizing system, a system of choice being initial reaction with NBS, followed by treatment with a base, such as basic alumina. Compound 28 is then converted to isoresibufogenin (a) by selective hydrogenation of the 3-position, in the same manner as in the final step of the preparation of isobufalin (a).

As previously stated, the preparation of isobufalin (b) is strictly analogous to that of isobufalin (b), and the preparation of isoresibufogenin (b) is strictly analogous to that of isobufalin (b), the difference being the reactive site of the furyl organo-metallic reagent and the consequent difference in the site of attachment of the furyl group.

The isobufalins and isoresibufogenins of this invention are readily converted to the corresponding 3-sugar compounds, i.e. to their glycosidic form, by standard reaction with the sugar of choice. Glucose is a preferred sugar, but other monosaccharide sugars, such as those found in naturally occurring cardiac glycosides, as well as polysaccharides, can be used. Such reactions are well known to those skilled in the art.

Within the scope of the invention there are also certain alternative synthetic routes which may be taken in the preparation of the novel compounds. Such alternatives involve the same key steps of allylic rearrangement and oxidative ring opening. For instance, in the preparation of isobufalin (a), an alternative and equivalent partial synthetic route from Compound 5 to Compound 13 is as follows (with the steroid nucleus shown only in partial form):

(a) reacting Compound 5 with chloromethyl ether in a standard reaction to produce a 15-diether aldehyde of Formula 30 (Compound 30)

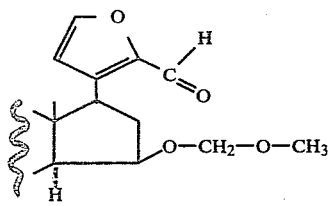

(b) reducing Compound 30 to produce an alcohol of Formula 31 (Compound 31), reaction conditions and variations being as in the conversion of Compound 5 to Compound 6

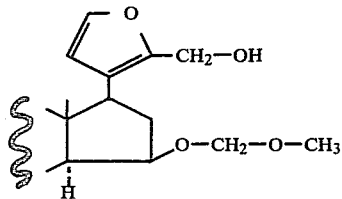

(c) oxidizing Compound 31 to produce a ketohemiacetal of Formula 32 (Compound 32), reaction conditions and variations being as in the conversion of Compound 6 to Compound 7

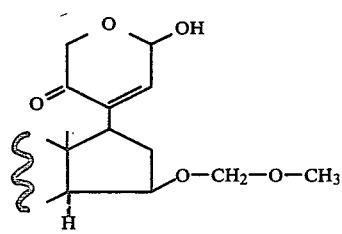

(d) oxidizing Compound 32 to produce a keto lactone intermediate, and reducing said intermediate to produce a hydroxylactone of Formula 33 (Compound 33), reaction conditions and variations being as in the conversion of Compound 10 to Compound 11

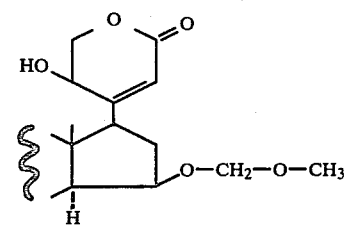

(e) dehydrating the 21-hydroxy of Compound 33 by substituting the hydroxy with a leaving group X″ to produce a substituted product of Formula 34 (Compound 34), reaction conditions and variations being as in the conversion of Compound 11 to Compound 12

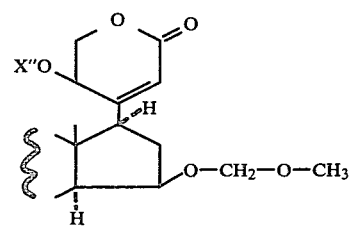

(f) eliminating the leaving group from Compound 34 to produce a pyrone derivative of Formula 35 (Compound 35), reaction conditions and variations being as in the conversion of Compound 12 to Compound 13

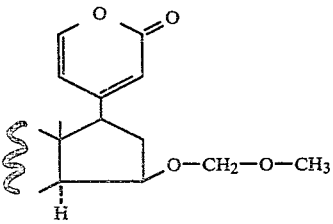

(g) replacing the diether group with a hydroxy group, by standard reaction in acid known to those skilled in the art, to yiedl the hydroxy pyrone of Formula 36 (Compound 36)

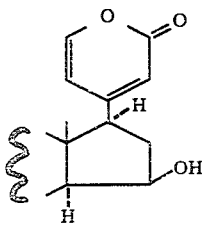

and
(h) dehydrating Compound 36 to produce Compound 13, reaction conditions and variations being as in the conversion of Compound 8 to Compound 9.

The above alternative and equivalent partial synthetic route can be used analogously in the preparation of other compounds of the invention.

The following Examples illustrate the method of the invention.

EXAMPLE 1

Isobufalin (a) can be prepared by the following synthetic procedure. The numbered compounds correspond to those defined above, where Z is the cyclic diether; X is benzyl; X' is acetate; X" is mesyl.

Conversion of Compound 1 to Compound 2 n-Butyllithium (2.74 ml, 2.1 M solution) was added to a stirred ether solution of 2-acetal-3-bromofuran (1.314 g in 20 ml of ether) at $-70°$ C. under nitrogen for 30 minutes after which the 17-$\alpha,\beta$-unsaturated ketone Compound 1 (1.87 g, in 10 ml of benzene and 20 ml of ether) was added and the solution was stirred for 30 minutes at the same temperature. The excess reagent was destroyed with water and the mixture washed with water, dried over anhydrous $MgSO_4$ and evaporated to dryness. The crude product was purified by column chromatography to get 2.48 g of pure tert-alcohol Compound 2 in 95%.

Mass spectrum: Calc. for $C_{33}H_{42}O_5$ 518; Found 518
I.R. ($CHCl_3$): 3600 cm$^{-1}$
N.M.R. ($CDCl_3$): $\tau=2.62$ (s, 6H, aromatic and 24-H), 3.71 (s, 1H, 22-H), 3.87 (d, J=2, 1H, 23-H), 3.85 (d, J=6, 1H, 15-H), 4.22 (dd, J=6, 2, 1H, 16-H), 5.5 (s, 2H, benzylic), 5.87 (m, 4H, dioxolane), 6.3 (broad s, 1H, 3$\alpha$-H), 8.97 (s, 3H, 18-$CH_3$), 9.0 (s, 3H, 19-$CH_3$).

Conversion of Compound 2 to Compound 3

The tert-alcohol Compound 2 (2.46 g) was acetylated with acetic anhydride (5 ml) in pyridine (10 ml) in the presence of 4-dimethylaminopyridine (116 mg) at room temperature for 3 days. The reaction mixture was evaporated at 50° C. in vacuo to dryness and worked up to get the crude acetate which was subjected to an allylic rearrangement in refluxling aqueous acetone (300 ml, 20% $H_2O$) in the presence of calcium carbonate (1.45 g) for four days. Worked up and chromatography on silica gel to get the secondary allylic alcohol Compound 3 (1.77 g, 83%).

Mass spectrum: Calc. for $C_{33}H_{42}O_5$ 518; Found 518
I.R. ($CHCl_3$): 3605 cm$^{-1}$ (OH)
N.M.R. ($CDCl_3$): $\tau=2.66$ (s, 6H, aromatic & 24-H), 3.63 (d, J=2, 23-H), 4.1 (s, 1H, 22-H), 4.13 (d, J=2, 1H, 16-H), 5.42 (broad s, 1H, 15-H), 5.49 (s, 2H, benzylic), 5.88 (m, 4H, dioxolane), 6.27 (broad s, 1H, 3$\alpha$-H), 8.76 (s, 3H, 18-$CH_3$), 8.97 (s, 3H, 19-$CH_3$).

Conversion of Compound 3 to Compound 4

The allylic alcohol Compound 3 (1.762 g) was hydrogenated in ethanol (50 ml) with 10% $Pd/CaCO_3$ (176 mg) at room temperature. Worked up and chromatographed on silica gel to the pure 15$\beta$-alcohol (1.54 g, 92%). Mass spectrum: Calc. for $C_{33}H_{44}O_5$ 520; Found 520
I.R. ($CHCl_3$): 3610, 3450 cm$^{-1}$ (OH)
I.R. ($CHCl_3$): $\tau=2.67$ (s, 6H, aromatic & 24-H), 3.63 (d, J=2, 1H, 23-H), 4.11 (s, 1H, 22-H), 5.5 (s, 2H, benzylic), 5.65 (t, J=7, 1H, 15-H), 5.92 (m, 4H, dioxolane), 6.27 (broad s, 1H, 3-H), 9.0 (s, 3H, 19-$CH_3$), 9.15 (s, 3H, 18-$CH_3$).

Conversion of Compound 4 to Compound 5

A mixture of Compound 4 (1.54 g in 18 ml of THF) and 2 ml of 1 N HCl was stirred at room temperature for 1 hour and then neutralized with aqueous $NaHCO_3$, extracted with ether, dried over anhydrous $MgSO_4$ and evaporated to dryness to get the crude product which was used for the next step without further purification.

Mass spectrum: Calc. for $C_{31}H_{40}O_4$ 476; Found 476
I.R. ($CHCl_3$): 3650, 3530 (OH), 1690 cm$^{-1}$ (>C=O)
N.M.R. ($CDCl_3$): $\tau=0.28$ (s, 1H, 22-H), 2.42 (d, J=2, 1H, 24-H), 2.66 (s, 5H, aromatic), 3.4 (d, J=2, 1H, 23-H), 5.5 (s, 2H, benzylic), 5.58 (t, J=7, 1H, 15-H), 6.25 (broad s, 1H, 3-H), 9.0 (s, 3H, 19-$CH_3$), 9.13 (s, 3H, 18-$CH_3$).

Conversion of Compound 5 to Compound 6

The crude aldehyde Compound 5 (1.41 g) in THF (10 ml) and methanol (1 ml) was reduced with sodium borohydride (225 mg) at room temperature. Worked up and chromatographed to get the pure primary alcohol Compound 6 (1.35 g, 95%).

Mass spectrum: Calc. for $C_{31}H_{42}O_4$ 478; Found 478
I.R. ($CHCl_3$): 3620, 3450 cm$^{-1}$ (OH)
N.M.R. ($CDCl_3$): $\tau=2.66$ (s, 6H, aromatic & 24-H), 3.67 (d, J=2, 1H, 23-H), 5.45 (broad s, 2H, 22-H), 5.5 (s, 2H, benzylic), 5.63 (t, J =7, 1H, 15-H), 6.25 (broad s, 1H, 3-H), 8.99 (s, 3H, 19-$CH_3$), 9.15 (s, 3H, 18-$CH_3$).

Conversion of Compound 6 to Compound 7

A mixture of the primary alcohol Compound 6 (1.35 g) and sodium acetate (324 mg) in dichloromethane (45 ml) was oxidized with m-chloroperbenzoic acid (718 mg) in ice-bath for 2 hours. The precipitate was filtered off through Celite and the filtrate washed successively with sodium thiosulfite, sodium bicarbonate and water. Dried over anhydrous $MgSO_4$ and evaporated to dryness to get the crude product which was purified by column chromatography and yielded the pure ketohemiacetal Compound 7 (1.25 g, 90%).

Mass spectrum: Calc. for $C_{31}H_{42}O_5$ 494; Found 494
I.R. (CHCl$_3$): 3600, 3360 (OH), 1690 (>C=O), 1640 cm$^{-1}$ (>C=C<)
N.M.R. (CDCl$_3$): $\tau=2.64$ (s, 5H, aromatic), 3.26 (d, J=3, 23-H), 4.3 (d, J=3, 24-H), 5.5 (s, 2H, benzylic), 5.65, 5.72 (q, J=17, 22-H), 6.27 (broad s, 1H, 3-H), 9.0 (s, 3H, 19-CH$_3$), 9.17, 9.23 (s, 3H, 18-CH$_3$).

Conversion of Compound 7 to Compound 8

A mixture of keto-hemiacetal Compound 7 (148 mg), sodium acetate (37 mg) and acetic anhydride (38.3 mg) in benzene (15 ml) was refluxed for 1 hour after which was cooled to room temperature and diluted with ether, washed with sodium bicarbonate and sodium chloride solution. The crude produce was purified by preparative TLC to get the keto-acetate Compound 8 (135 mg, 90%).

Mass spectrum: Calc. for $C_{33}H_{44}O_6$ 536; Found 536
I.R. (CHCl$_3$): 3610, 3460 (OH, 1750, 1690 (>C=O), 1640 cm$^{-1}$ (>C=C<)
N.M.R. (CDCl$_3$): $\tau=2.65$ (s, 5H, aromatic), 3.28 (d, J=4, 1H, 23-H), 3.42 (d, J=2, 1H, 24-H), 5.5 (s, 2H, benzylic), 5.65 (q, J=17, 2H, 22-H), 5.67 (t, J=6, 1H, 15-H), 6.25 (broad s, 1H, 3-H), 7.87

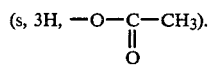

(s, 3H, —O—C—CH$_3$).

9.0 (s, 3H, 19-CH$_3$), 9.18, 9.22 (s, 3H, 18-CH$_3$).

Conversion of Compound 8 to Compound 9

The keto-acetate Compound 8 (135 mg) in pyridine (1 ml) was cooled in ice-bath and treated with thionyl chloride (38 mg) for 1 hour. Worked up and purified by preparative TLC to get the 14-dehydro-keto-acetate Compound 9 (114 mg, 88%).

Mass spectrum: Calc. for $C_{33}H_{42}O_5$ 518; Found 518
I.R. (CHCl$_3$): No hydroxyl absorption. 1745, 1690 (>C=O), 1640 cm$^{-1}$ (>C=C<)
N.M.R. (CDCl$_3$): $\tau=2.67$ (s, 5H, aromatic), 3.27 (d, J=4, 1H, 23-H), 3.46 (d, J=2, 1H, 24-H), 4.77 (broad s, 1H, 15-H), 5.5 (s, 2H, benzylic), 5.64 (q, J=17, 2H, 22-H), 6.28 (broad s, 1H, 3-H), 7.88

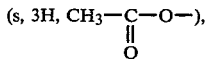

(s, 3H, CH$_3$—C—O—), 9.03 (s, 3H, 19-CH$_3$), 9.27, 9.31 (s, 3H, 18-CH$_3$).

Conversion of Compound 9 to Compound 10

The 14-dehydro-keto-acetate Compound 9 (110 mg) in THF(92.7 ml) was hydrolyzed with aqueous KOH (1 N, 0.3 ml) at room temperature for 1 hour after which the solution was carefully neutralized with dilute HCl solution, extracted with ether, washed with sodium chloride solution, dried over anhydrous MgSO$_4$ and evaporated to dryness. The crude product was purified by preparative TLC to get the pure 14-dehydro-keto-hemiacetal Compound 10 (90 mg, 90%).

Mass spectrum: Calc. for $C_{31}H_{40}O_4$ 476; Found 476
I.R. (CHCl$_3$): 3590, 3350 (OH), 1690 (>C=O), 1640 cm$^{-1}$ (>C=C<)
N.M.R. (CDCl$_3$): $\tau=2.63$ (s, 5H, aromatic), 3.24 (d, J=3, 1H, 23-H), 4.33 (broad s, 1H, 24-H), 4.77 (broad s, 1H, 15-H), 5.49 (s, 2H, benzylic), 5.65, 5.7 (q, J=17, 2H, 22-H), 6.27 (broad s, 1H, 3-H), 9.03 (s, 3H, 19-CH$_3$), 9.26, 9.31 (s, 3H, 18-CH$_3$).

Conversion of Compound 10 to Compound 11

A dichloromethane solution of the 14-dehydro-keto-hemiacetal Compound 10 (60 mg in 1.5 ml of CH$_2$Cl$_2$) was added to a stirred solution of CrO$_3$-2 pyridine complex (195 mg in 10 ml CH$_2$Cl$_2$) at room temperature. Ten minutes after the addition, the excess reagent was destroyed with 10 ml of ether and the precipitate was filtered off through Celite. The filtrate was evaporated to 5 ml volume which was then cooled in ice-bath and reduced with excess Zn(BH$_4$)$_2$ ether solution. Stirred for 1 hour, the excess reagent was destroyed with minimum amount of water and filtered off the precipitate through Celite. The filtrate was evaporated to dryness and purified by preparative TLC to get the pure hydroxy lactone Compound 11 (49 mg. 80%).

Mass Spectrum: Calc. for $C_{31}H_{40}O_4$ 476; Found 476
I.R. (CHCl$_3$): 3580, 3400 (OH), 1710 (>C=O), 1630 cm$^{-1}$ (>C=C<)
N.M.R. (CDCl$_3$): $\tau=2.64$ (s, 5H, aromatic), 4.07 (d, J=4, 1H, 23-H), 4.73 (broad s, 1H, 15-H), 5.49 (s, 2H, benzylic), 5.59 (d, J=4, 2H, 22-H), 5.84 (broad s, 1H, 21-H), 6.27 (broad s, 1H, 3-H), 9.01 (s, 3H, 19-CH$_3$), 9.14, 9.2 (s, 3H, 18-CH$_3$).

Conversion of Compound 11 to Compound 12

The hydroxy-lactone Compound 11 (90 mg) in dichloromethane (2 ml) and triethylamine (1 ml) was cooled in ice-bath and treated with mesyl chloride (30 mg). The mixture was stirred in ice-bath for 30 minutes and then diluted with dichloromethane, washed with 5% citric acid, 5% NaHCO$_3$ solution, dried over anhydrous MgSO$_4$ and evaporated to dryness. The crude product was purified by preparative TLC to get the pure mesylate Compound 12 (90 mg, 80%).

Mass spectrum: Calc. for $C_{32}H_{42}O_5S$ 554; Found 554
I.R. (CHCl$_3$): No hydroxyl absorption. 1725, (>C=O), 1630 (<C=C>), 1345, 1165 cm$^{-1}$ (O—SO$_2$—)
N.M.R. (CDCl$_3$): $\tau=2.66$ (s, 5H, aromatic), 3.85 (d, J=4, 1H, 23-H), 4.79 (broad s, 2H, 15-H and 21-H), 5.5 (s, 2H, benzylic), 6.25 (broad s, 1H, 3-H), 6.87 (s, 3H, mesylate), 9.02 (s, 3H, 19-CH$_3$), 9.12, 9.18 (s, 3H, 18-CH$_3$).

Conversion of Compound 12 to Compound 13

A mixture of mesylate Compound 12 (90 mg) and DBN (60.5 mg) in benzene (4 ml) was refluxed for 1 hour. Worked up and purified by preparative TLC to get the pure 3$\beta$-benzyloxy-14-dehydroisobufalin Compound 13 (64 mg, 86%) which was recrystallized from ether-CHCl$_3$, m.p. 144°-5° C.

Mass spectrum: Calc. for $C_{31}H_{38}O_3$ 458; Found 458
I.R. (CHCl$_3$): 1720 (>C=O), 1635 cm$^{-1}$ (>C=C<)
N.M.R. (CDCl$_3$): $\tau=2.59$ (d, J=5, 1H, 22-H), 2.67 (s, 5H, aromatic), 3.82 (s, 1H, 23-H), 3.87 (d, J=5, 1H, 21-H), 4.76 (broad s, 1H, 15-H), 5.5 (s, 2H, benzylic), 6.28 (broad s, 1H, 3-H), 9.02 (s, 3H, 19-CH$_3$), 9.25 (s, 3H, 18-CH$_3$).

Conversion of Compound 13 to Compound 14

The 14-dehydroisobufalin Compound 13 (46 mg) in 2 ml of aqueous acetone (4 ml, 10% H$_2$O) was treated with NBS (22.3 mg) and 1% HClO$_4$ (1 drop) at room temperature for 30 minutes. After the addition of aqueous sodium sulfite, the reaction mixture was evaporated under reduced pressure at room temperature to remove most of the solvent. The residue was extracted with dichloromethane, washed with water, dried over anhydrous MgSO$_4$ and evaporated to 2 ml to which Raney nickel (1 g) was added and stirred for 1 hour at room temperature. Raney nickel was filtered off and the filtrate was evaporated to get the crude product which was purified by preparative TLC and yielded the pure 3β-benzyloxyisobufalin Compound 14 (34 mg. 72%) which was recrystallized from ether-chloroform and melted at 215°–7° C.

Mass spectrum: Calc. for C$_{31}$H$_{40}$O$_4$ 476; Found 476

I.R. (CHCl$_3$): 3610, 3460 (OH), 1720 (>C=O), 1635 cm$^{-1}$ (>C=C<)

N.M.R. (CDCl$_3$): τ=2.58 (d, J=5, 1H, 22-H), 2.62 (s, 5H, aromatic), 3.28 (dd, J=2, 6, 1H, 21-H), 3.85 (broad s, 1H, 23-H), 5.47 (s, 2H, benzylic), 6.25 (broad s, 1H, 3-H), 9.04 (s, 3H, 19-CH$_3$), 9.22 (s, 3H, 18-CH$_3$).

Conversion of Compound 14 to Compound 15

The 3β-benzyloxyisobufalin Compound 14 (30 mg) in ethanol-benzene mixture (1 ml benzene, 4 ml ethanol) was hydrogenated over 10% Pd/C (6 mg) at room temperature and normal pressure. The catalyst was filtered through Celite and the filtrate was evaporated to give the crude product which was purified by preparative TLC and yielded the pure isobufalin Compound 15 (17.6 mg, 88%) and starting material (5.6 mg). The isobufalin 15 was recrystallized from ether-CHCl$_3$ and melted at 128°–9° C.

Mass spectrum: Calc. for C$_{24}$H$_{34}$O$_4$ 386; Found 386

I.R. (CHCl$_3$): 3610, 3450 (OH), 1720 (>C=O), 1635 cm$^{-1}$ (>C=C<)

N.M.R. (CDCl$_3$): τ=2.65 (d, J=5, 1H, 22-H), 3.44 (dd, J=2.6, 1H, 21-H), 3.92 (s, 1H, 23-H), 5.89 (broad s, 1H, 3-H), 9.05 (s, 3H, 19-CH$_3$), 9.23 (s, 3H, 18-CH$_3$).

EXAMPLE 2

Isoresibufogenin (a) can be prepared by first synthesizing Compound 13, as in Example 1, and then converting Compound 13, in a two-step process, to the final product. The numbered compounds correspond to those defined above, where X is benzyl.

Conversion of Compound 13 to Compound 16

The 14-dehydroisobufalin (30 mg) in aqueous acetone (1.5 ml, 10% H$_2$O) was treated with NBS (15 mg) and 1% HClO$_4$ (1 drop) at room temperature for 30 minutes. Worked up and the crude bromohydrin in dichloromethane (2 ml) was stirred with basic alumina at room temperature for 30 minutes after which the alumina was filtered off and the filtrate evaporated to dryness. The crude product was purified by preparative TLC to yield the pure 14β,15β-epoxide Compound 16 (26 mg, 85%) which was recrystallized from ether-chloroform and melted at 197°–8° C.

Mass spectrum: Calc. for C$_{31}$H$_{38}$O$_4$ 474; Found 474

I.R. (CHCl$_3$): 1719 (>C=O), 1630 cm$^{-1}$ (>C=C)

N.M.R. (CDCl$_3$): τ=2.66 (s, 6H, aromatic and 22-H), 3.34 (dd, J=2, g, 1H, 21-H, 3.95 (broad s, 1H, 23-H), 5.51 (s, 2H, benzylic), 6.27 (broad s, 1H, 3-H), 6.47 (s, 1H, 15-H), 9.01 (s, 3H, 19-CH$_3$), 9.15 (s, 3H, 18-CH$_3$).

Conversion of Compound 16 to Compound 17

The 3β-benzyloxy isoresifubogenin Compound 16 (20 mg) in ethanol-benzene mixture (1 ml benzene, 4 ml ethanol) was hydrogenated over 10% Pd/C (5 mg). After work up and purification it yielded the isoresibufogenin Compound 17 (11.6 mg, 84%) and starting material (3 mg).

The isoresibufogenin was recrystallized from CHCl$_3$-n-hexane and melted at 210°–2° C.

Mass spectrum: Calc. for C$_{24}$H$_{34}$O$_4$ 384; Found 384

I.R. (CHCl$_3$): 3605, 3420 (OH), 1710 (>C=O), 1630 cm$^{-1}$ (>C=C<)

N.M.R. (CDCl$_3$): τ=2.61 (d, J=5, 1H, 22-H), 3.3 (dd, J=2, 6, 1H, 21-H), 3.93 (s, 1H, 23-H), 5.87 (broad s, 1H, 3-H), 6.47 (s, 1H, 15-H), 9.0 (s, 3H, 19-CH$_3$), 9.16 (s, 3H, 18-CH$_3$).

EXAMPLE 3

Isobufalin (a) glucoside can be prepared from isobufalin (a) by reaction with tetra-O-acetyl-α-D-glucopyranosl bromide to yield the acetylated glucoside, followed by deacetylation to yield the final product. Isobufalin (a) (0.15 m mole) is mixed with 1,2-dichloroethane (approximately 5 ml), dry silver oxide (approximately 139 mg), and anhydrous MgSO$_4$ (approximately 280 mg) and stirred 1 hour at room temperature. Tetra-O-acetyl-α-D-glycopyranosyl bromide (approximately 185 mg) in 1,2-dichloroethane (approximately 1 ml) is added dropwise and stirred 24 hours. The mixture is filtered, evaporated and purified by TLC and crystallization (chloroform/ethyl ether) to give 3β-(tetra-O-acetyl-β-D-glucopyranosyl).

The acetylated glucoside is converted to the final product by allowing approximately 2 grams to stand 15 hours at 4° C. in a mixture of methylene chloride (6 ml), methanol (30 ml) and methanol saturated with anhydrous ammonia (60 ml). The solution is evaporated and the isobufalin (a) glucoside product is purified by crystallization from methanol/ethyl ether.

We claim:

1. A compound having the general formula

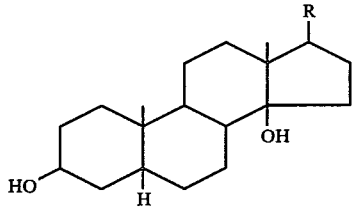

wherein R is selected from the group consisting of

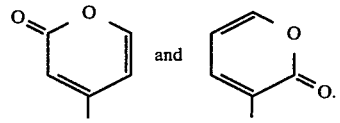 and

2. A compound having the general formula

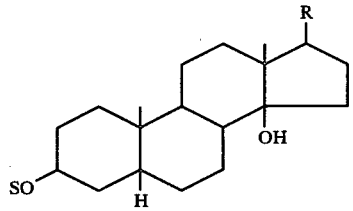

wherein R is selected from the group consisting of

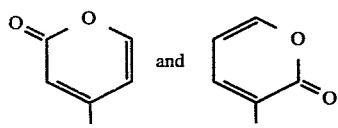 and and wherein S is selected from the group consisting of sugars.
3. A compound as in claim 2, wherein S is glucose.
4. A compound having the general formula

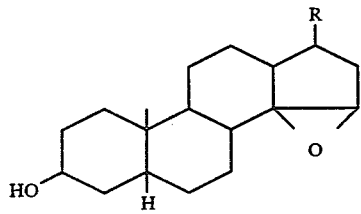

wherein R is selected from the group consisting of

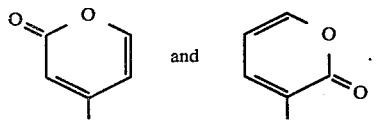 and

5. A compound having the general formula

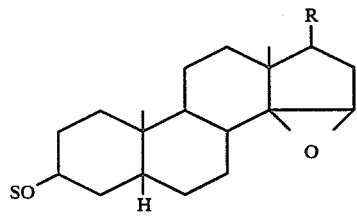

wherein R is selected from the group consisting of

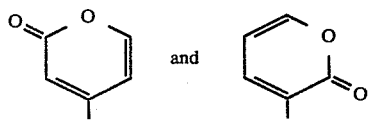 and and wherein S is selected from the group consisting of sugars.
6. A compound as in claim 5, wherein S is glucose.
7. A method of preparing isobufalin (a) of formula

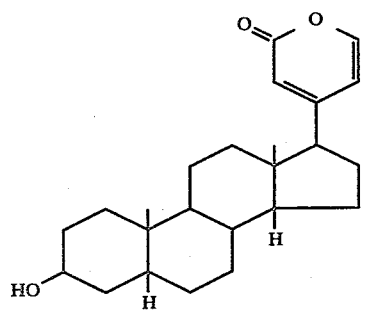

comprising the steps of:
(a) reacting a compound having the formula

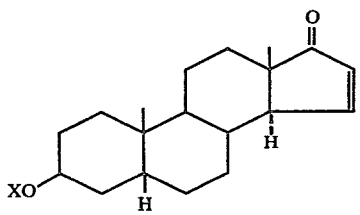

wherein X is a blocking group, with an anion of formula

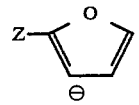

where Z is selected from the group consisting of

and CH$_3$—O—CH$_2$—O—CH$_2$—, to produce a tertiary alcohol having the formula

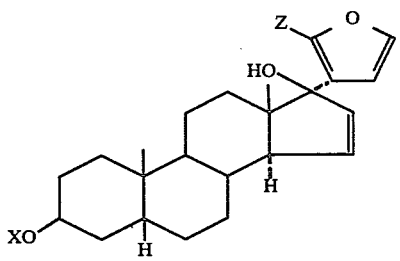

(b) acetylating said tertiary alcohol and subjecting the resulting 17-acetate to treatment with base in organic solution to produce an allylic alcohol having the formula

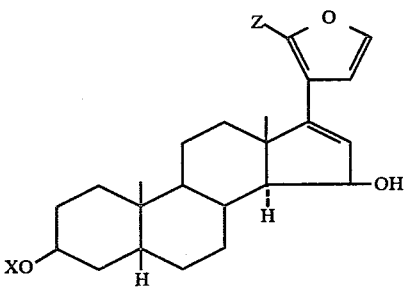

(c) selectively hydrogenating the 16,17 double bond of said allylic alcohol by hydrogenating over a hydrogenation catalyst containing a metal from the platinum group to produce a 16,17 saturated ketal;
(d) hydrolyzing said 16,17 saturated ketal in acid conditions to produce a furyl aldehyde, and then reducing said furyl aldehyde with a hydride reducing agent to produce a furyl methylene alcohol having the formula

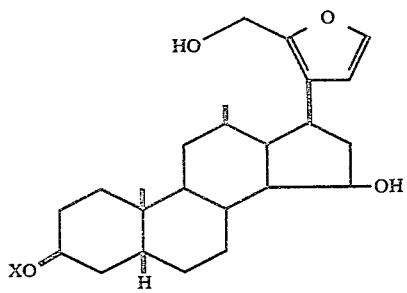

(e) oxidizing said furyl methylene alcohol to produce a 23-hydroxy ketohemiacetal having the formula

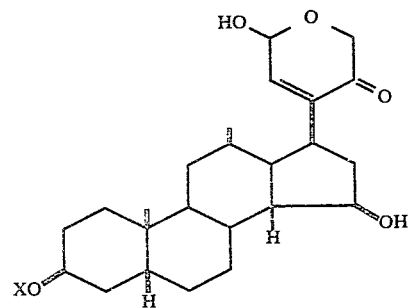

and then converting said ketohemiacetal to isobufalin (a).

8. The method of claim 7, wherein said conversion of said ketohemiacetal to isobufalin (a) comprises the following steps:

(f) substituting the 23-hydroxy group with a hydrolyzable blocking group; selectively dehydrating the 15-position to produce a 14,15 unsaturated compound; and selectively hydrolyzing the 14,15 unsaturated compound in basic conditions to produce a 23-hydroxy compound having the formula

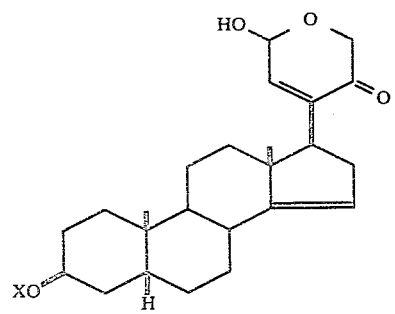

(g) oxidizing said 23-hydroxy compound to produce a keto lactone intermediate, and reducing said intermediate with a hydride reducing agent to produce a 21-hydroxy lactone having the formula

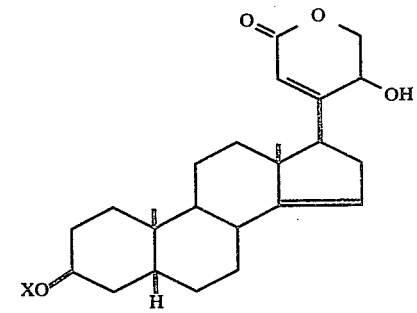

(h) dehydrating the 21-hydroxy lactone to produce a pyrone derivative having the formula

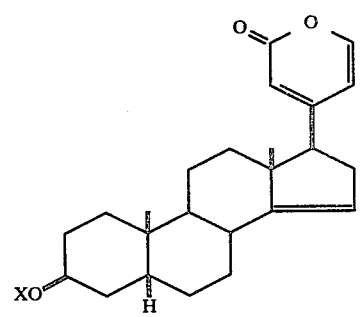

(i) hydroxylating said pyrone derivative at the 14-position, using a stereospecific hydroxylating agent selected from the group consisting of N-bromosuccinimide and N-bromoacetamide, to produce a precursor of isobufalin (a) having the formula

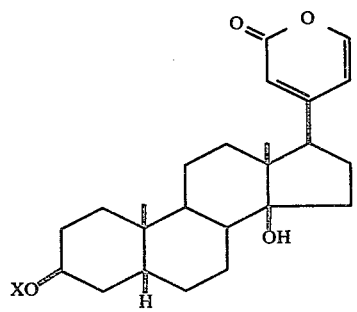

and, (j) selectively converting the 3-position blocking group of said precursor into a hydroxy group, thereby yielding isobufalin (a).

9. A method of preparing isobufalin (b) of the formula

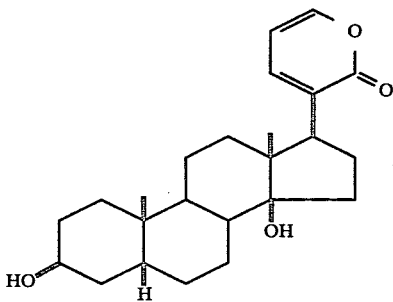

comprising the steps of:
(a) reacting a compound having the formula

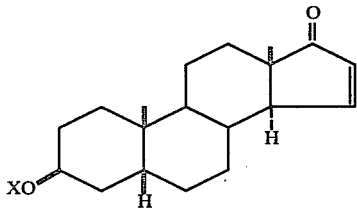

wherein X is a blocking group, with an anion of formula

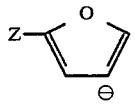

where Z is selected from the group consisting of

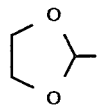

and $CH_3-O-CH_2-O-CH_2-$, to produce a tertiary alcohol having the formula

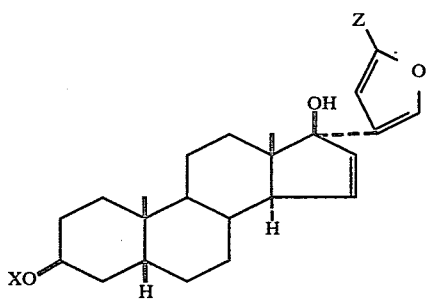

(b) acetylating said tertiary alcohol and subjecting the resulting 17-acetate to treatment with base in organic solution to produce an allylic alcohol having the formula

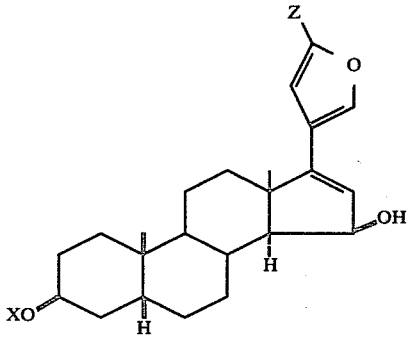

(c) selectively hydrogenating the 16,17 double bond of said allylic alcohol by hydrogenating over a hydrogenation catalyst containing a metal from the platinum group to produce a 16,17 saturated ketal;
(d) hydrolyzing said 16,17 saturated ketal in acid conditions to produce a furyl aldehyde, and then reducing said furyl aldehyde with a hydride reducing agent to produce a furyl methylene alcohol having the formula

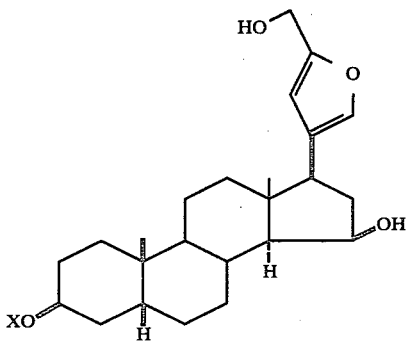

(e) oxidizing said furyl methylene alcohol to produce a 21-hydroxy ketohemiacetal having the formula

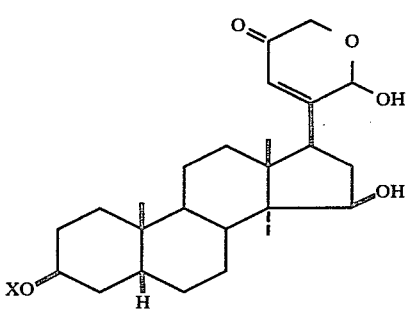

and then converting said ketohemiacetal to isobufalin (b).

10. The method of claim 9, wherein said conversion of said ketohemiacetal to isobufalin (b) comprises the following steps:
(f) substituting the 21-hydroxy group with a blocking group; selectively dehydrating the 15-position to produce a 14,15-unsaturated compound; and selectively hydrolyzing the 14,15-unsaturated compound in basic conditions to produce a 21-hydroxy compound having the formula

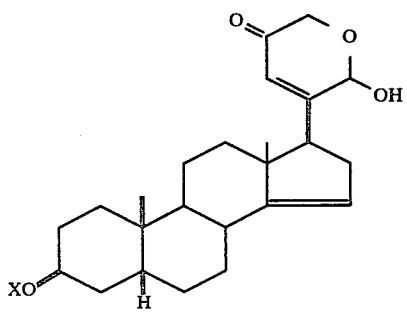

(g) oxidizing said 21-hydroxy compound to produce a keto lactone intermediate, and reducing said intermediate with a hydride reducing agent to produce a hydroxy lactone having the formula

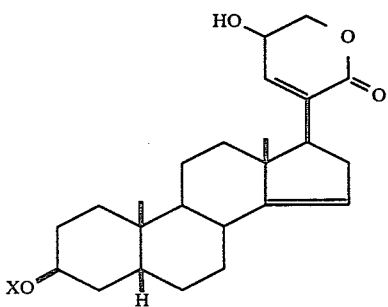

(h) dehydrating the 21-hydroxy to produce a pyrone derivative having the formula

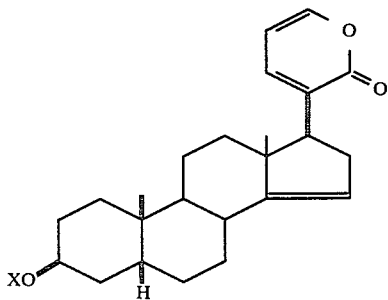

(i) hydroxylating said pyrone derivative at the 14-position, using a stereospecific hydroxylating agent selected from the group consisting of N-bromosuccinimide and N-bromoacetamide, to produce a precursor of isobufalin (b) having the formula

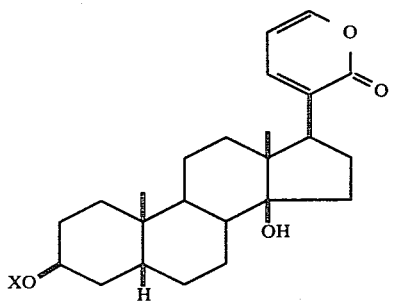

(j) selectively converting the 3-position blocking group of said precursor into a hydroxy group, thereby yielding isobufalin (b).

11. A method of preparing isoresibufogenin (a) of the formula

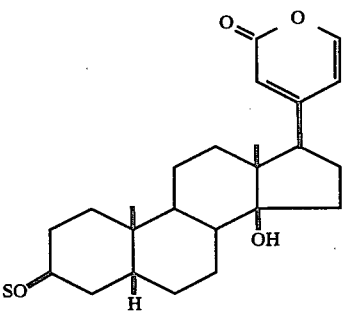

comprising the steps of
(a) reacting a compound having the formula

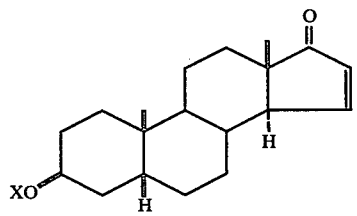

, wherein X is a blocking group, with an anion of formula

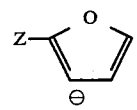

, where Z is selected from the group consisting of

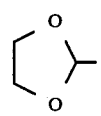

and $CH_3-O-CH_2-O-CH_2-$, to produce a tertiary alcohol having the formula

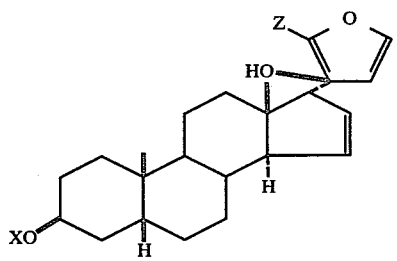

(b) acetylating said tertiary alcohol and subjecting the resulting 17-acetate to treatment with base in organic solution to produce an allylic alcohol having the formula

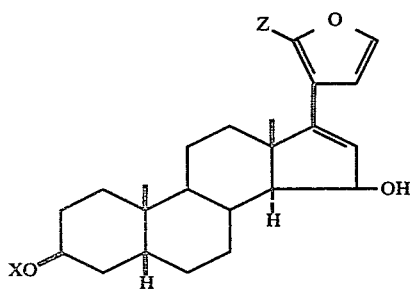

(c) selectively hydrogenating the 16,17 double bond of said allylic alcohol by hydrogenating over a hydrogenation catalyst containing a metal from the platinum group to produce a 16,17 saturated ketal;

(d) hydrolyzing said 16,17 saturated ketal in acid conditions to produce a furyl aldehyde, and then reducing said furyl aldehyde with a hydride reducing agent to produce a furyl methylene alcohol having the formula

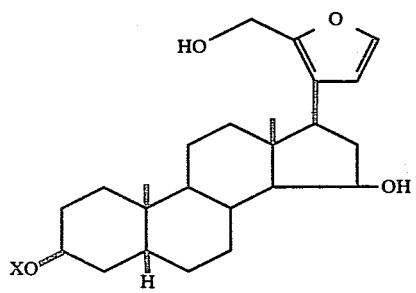

(e) oxidizing said furyl methylene alcohol to produce a 23-hydroxy ketohemiacetal having the formula

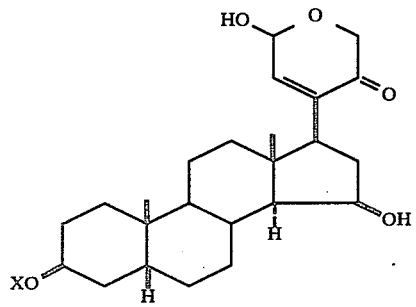

and then converting said ketohemiacetal to isoresibufogenin (a).

12. The method of claim 11 wherein said conversion of said ketohemiacetal to isoresibufogenin (a) comprises the following steps:

(f) substituting the 23-hydroxy group with a hydrolyzable blocking group; selectively dehydrating the 15-position to produce a 14,15-unsaturated compound; and selectively hydrolyzing the 14,15-unsaturated compound in basic conditions to produce a 23-hydroxy compound having the formula

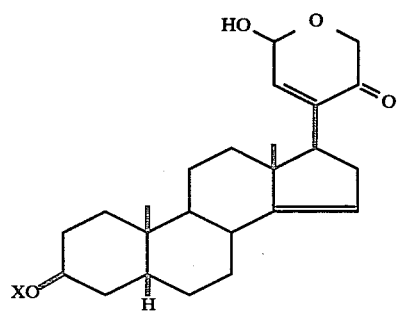

(g) oxidizing said 23-hydroxy compound to produce a keto lactone intermediate, and reducing said intermediate with a hydride reducing agent to produce a 21-hydroxy lactone having the formula

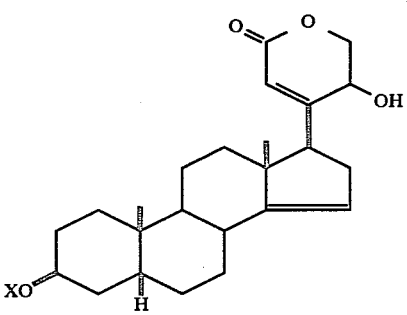

(h) dehydrating the 21-hydroxy lactone to produce a pyrone derivative having the formula

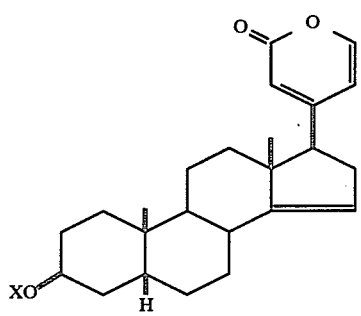

(i) epoxidizing said pyrone derivative at the 14,15-position to produce a precursor of isoresibufogenin (a) having the formula

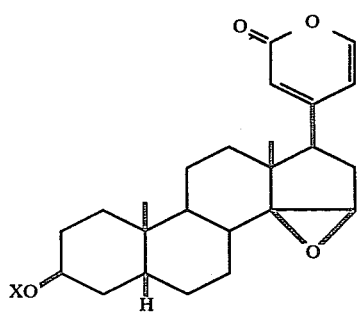

and, (j) selectively convering the 3-position blocking group of said precursor into a hydroxy group, thereby yielding isoresibufogenin (a).

13. A method of preparing isoresibufogenin (b) of the formula

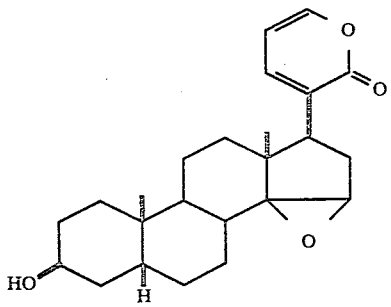

comprising the steps of
(a) reacting a compound having the formula

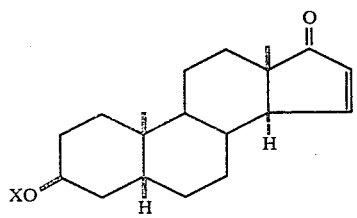

, wherein X is a blocking group, with an anion of formula

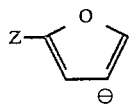

, where Z is selected from the group consisting of

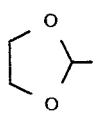

and CH₃—O—CH₂—O—CH₂—, to produce a tertiary alcohol having the formula

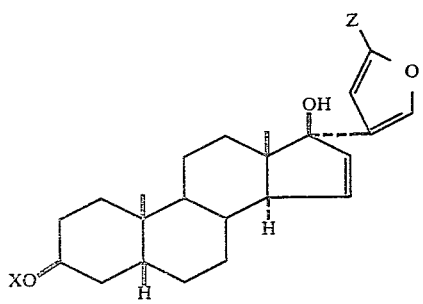

(b) acetylating said tertiary alcohol and subjecting the resulting 17-acetate to treatment with base in organic solution to produce an allylic alcohol having the formula

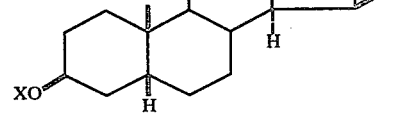

(c) selectivey hydrogenating the 16,17 double bond of said allylic alcohol by hydrogenating over a hydrogenation catalyst containing a metal from the platinum group to produce a 16,17 saturated ketal;
(d) hydrolyzing said 16,17 saturated ketal in acid conditions to produce a furyl aldehyde, and then reducing said furyl aldehyde with a hydride reducing agent to produce a furyl methylene alcohol having the formula

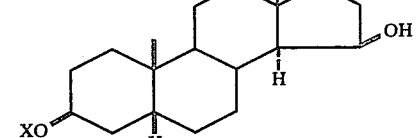

(e) oxidizing said furyl methylene alcohol to produce a 21-hydroxy ketohemiacetal having the formula

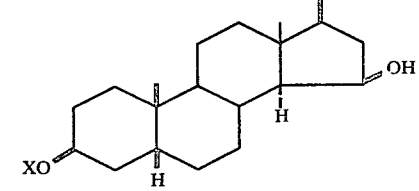

and then converting said ketohemiacetal to isoresibufogenin (b).

14. The method of claim 13, wherein said conversion of said ketohemiacetal to isoresibufogenin (b) comprises the following steps:
(f) substituting the 21-hydroxy group with a blocking group; selectively dehydrating the 15-position to produce a 14,15-unsaturated compound; and selectively hydrolyzing the 14,15-unsaturated compound in basic conditions to produce a 21-hydroxy compound having the formula

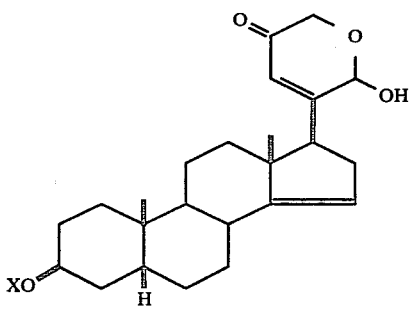

(g) oxidizing said 21-hydroxy compound to produce a keto lactone intermediate, and reducing said intermediate with a hydride reducing agent to produce a hydroxy lactone having the formula

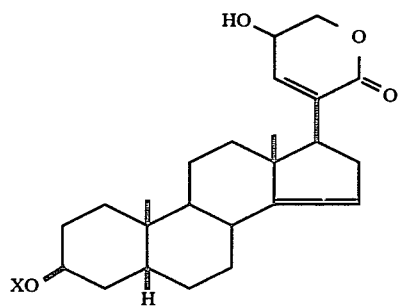

(h) dehydrating the 21-hdroxy to produce a pyrone derivative having the formula

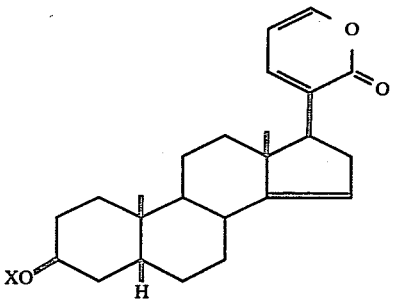

(i) epoxidizing said pyrone derivative at the 14,15-position to produce a precursor of isoresibufogenin (b) of formula

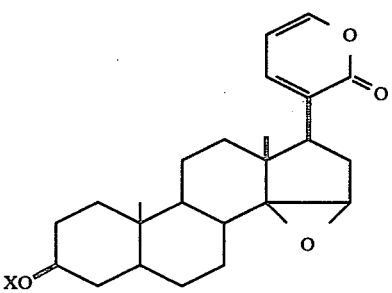

and, (j) selectively converting the 3-position blocking group of said precursor into a hydroxy group, thereby yielding isoresibufogenin (b).

* * * * *